United States Patent
Demarest et al.

(10) Patent No.: US 6,361,752 B1
(45) Date of Patent: Mar. 26, 2002

(54) APPARATUS FOR VOLATILIZING AND DISPENSING A CHEMICAL INTO A ROOM ENVIRONMENT

(75) Inventors: Scott W. Demarest, Caledonia; Imre J. Danes, Greenfield; David J. Houser, Racine, all of WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 09/314,805

(22) Filed: May 19, 1999

(51) Int. Cl.[7] ............... A61L 9/00; H02K 1/32; F28D 15/00; F24F 6/08
(52) U.S. Cl. .............. 422/306; 422/307; 310/64; 310/254; 165/104.26; 392/395; 392/403
(58) Field of Search .............. 422/5, 122–125, 422/305, 306, 307; 239/44, 47, 54–57, 60; 310/62, 63, 5, 64, 254, 52; 431/325; 502/400; 165/104–26; 392/390, 395, 391–392, 403

(56) References Cited

U.S. PATENT DOCUMENTS

| | | | |
|---|---|---|---|
| 2,561,890 A | 7/1951 | Stoddard | 103/118 |
| 2,614,820 A * | 10/1952 | Boydjieff | 261/26 |
| 3,294,994 A | 12/1966 | Anderson | 310/82 |
| 3,334,253 A | 8/1967 | Hill | 310/82 |
| 3,452,227 A | 6/1969 | Welch | 310/82 |
| 3,558,944 A | 1/1971 | Verge | 310/82 |
| 3,577,049 A | 5/1971 | Madurski et al. | 318/138 |
| 3,792,295 A | 2/1974 | Garbi | 310/46 |
| 3,803,431 A * | 4/1974 | Inaba et al. | 310/49 |
| 3,948,445 A * | 4/1976 | Andeweg | 239/53 |
| 3,990,848 A * | 11/1976 | Corris | 21/126 |
| 4,002,378 A | 1/1977 | Meinke | 308/147 |
| 4,102,656 A * | 7/1978 | Koritz | 55/210 |
| 4,145,001 A | 3/1979 | Weyenberg et al. | 239/56 |
| 4,161,283 A | 7/1979 | Hyman | 239/55 |
| 4,294,493 A | 10/1981 | Sindlinger et al. | 308/10 |
| 4,353,602 A | 10/1982 | Habermann | 308/10 |
| 4,367,424 A | 1/1983 | Pressley | 310/82 |
| 4,482,828 A | 11/1984 | Vergues et al. | 310/83 |
| 4,634,614 A | 1/1987 | Holzner | 428/35 |
| 4,695,434 A * | 9/1987 | Spector | 422/116 |
| 4,695,435 A * | 9/1987 | Spector | 422/124 |
| 4,728,837 A | 3/1988 | Bhadra | 310/80 |
| 4,734,606 A | 3/1988 | Hajec | 310/90.5 |
| 4,749,898 A | 6/1988 | Suzuki et al. | 310/114 |
| 4,755,709 A | 7/1988 | DeJager | 310/90.5 |
| 4,837,470 A | 6/1989 | Tamura | 310/82 |
| 4,849,606 A | 7/1989 | Martens, III et al. | 219/271 |
| 5,038,394 A * | 8/1991 | Hasegawa et al. | 392/395 |
| 5,121,881 A | 6/1992 | Lembeck | 239/44 |

(List continued on next page.)

FOREIGN PATENT DOCUMENTS

| | | |
|---|---|---|
| EP | 0 807 442 A2 | 11/1997 |
| EP | 0 882 459 A1 | 12/1998 |

OTHER PUBLICATIONS

Patent Abstracts of Japan, Publication No. 07163646.

Primary Examiner—Robert J. Warden, Sr.
Assistant Examiner—Monzer Chorbaji (57) ABSTRACT

An air quality modification apparatus for dispensing a volatile material, such as for scenting the air, controlling pests, allergen control, or the like, includes an electric motor having a rotor and a coil. When electric current is applied, the coil produces both heat and an electromagnetic field that causes rotation of the rotor. A source of the volatile material is located adjacent to the coil so as to be volatilized by the coil's heat. An impeller, attached to the rotor, moves air across the volatile material and blows the vapors away from the apparatus. Energy efficiency is provided by employing the electric motor coil as the source of heat to vaporize the volatile material. Also disclosed is a refill supply of a volatile material for use with such an air quality modification apparatus.

41 Claims, 4 Drawing Sheets

U.S. PATENT DOCUMENTS

| | | |
|---|---|---|
| 5,142,932 A | 9/1992 | Moya et al. .................. 74/479 |
| 5,155,402 A | 10/1992 | Bichler ...................... 310/90.5 |
| 5,237,234 A | 8/1993 | Jebens et al. ............... 310/309 |
| 5,311,091 A | 5/1994 | Maudal ....................... 310/90 |
| 5,397,220 A * | 3/1995 | Akihisa et al. ............. 417/369 |
| 5,419,879 A * | 5/1995 | Vlahakis et al. ............ 422/305 |
| 5,591,395 A | 1/1997 | Schroeder et al. ............. 433/4 |
| 5,647,053 A | 7/1997 | Schroeder et al. ........... 392/390 |
| 5,672,923 A | 9/1997 | Jacobsen et al. ............... 310/82 |
| 5,700,430 A | 12/1997 | Bonnema et al. ........... 422/125 |
| D403,419 S | 12/1998 | Davis .......................... 23/366 |
| 6,062,425 A * | 5/2000 | Brown et al. .................. 222/1 |

\* cited by examiner

APPARATUS FOR VOLATILIZING AND DISPENSING A CHEMICAL INTO A ROOM ENVIRONMENT

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

The present invention relates to devices that volatilize a substance and disperse the resultant vapor into the air in a room or other space; and more particularly to such devices for dispensing air scents, pest control materials, allergen control ingredients, and other substances for air quality modification.

A common type of air freshener is plugged into an electrical wall outlet to supply power to a heating coil within a housing. The generated heat raises the temperature of a fragrant substance and volatilizes the substance. Convection air currents dispense the fragrance into the room. A similar heating mechanism can be used with a liquid air freshener, as is described in U.S. Pat. Nos. 5,591,395 and 5,647,053. The disclosure of these patents and all other publications referred to herein are incorporated herein by reference as if fully set forth.

Both these types of air fresheners rely on existing air currents in the room to disperse the fragrance, and such reliance may not evenly or swiftly distribute the substance throughout a relatively large room. There is a need for efficient and economical means to both volatilize and effectively distribute volatilizable materials into the air of a room or other area.

SUMMARY OF THE INVENTION

The present environment control apparatus volatilizes and dispenses material into the air in a room or other area. This apparatus has an electric motor with a rotor and a coil such that, when electric current is applied to the coil, an electromagnetic field is produced that causes rotation of the rotor. Heat also is emitted from the coil. A source of volatile material to be dispersed into the ambient air is located adjacent the electric motor so as to be heated by the coil. That heating results in the material being volatilized. An air propulsion element, for example a fan or other impeller, is driven by the rotor to move air across the material and blow the resultant vapor into the surrounding environment. Various different embodiments of this apparatus can be provided for solid and liquid forms of the volatile material. In these various embodiments, the motor coil is configured to optimize heating of the material as well as applying a magnetic field to operate the motor.

For purposes of this disclosure, the term "magnet" means a member or material that already has been magnetized, either permanently or temporarily, so as to produce a magnetic field, such as an electromagnet or a permanent magnet. In contrast, the term "magnetic" means a member or material that has a sufficient magnetic susceptibility to be capable of being temporarily magnetized to form an electromagnet or capable of being magnetized to form a permanent magnet.

The electric motor of the apparatus can be either a nutating type motor or a more conventional, non-nutating motor. However, a nutating motor is preferred, in part because of the flexibility possible in the design of the core. For example but without limitation, the coil can have a serpentine shape. The air propulsion element referred to can be any air movement impeller but preferably is a fan of any convenient design. A simple propeller-type blade fan is especially preferred. The existence in the prior art is acknowledged of nutational motors that employ a rotor caused to nutate within a stator by application of an alternating magnetic field.

The volatile material can be any desired volatile material that most readily vaporizes at a temperature elevated above room temperature. Air quality modification agents, pest control ingredients, and allergen control agents are preferred. An air quality modification agent is defined as any volatile material that changes the scent or other quality of the air, including but not limited to perfumes and air deodorizers. Pest control ingredients include insecticides, growth regulators, repellents, and any other volatile material that kills or affects the development, functioning, or behavior of a pest animal, including but not limited to insects.

The source of a volatile material can include a carrier substance into which the volatile material is incorporated, whether by impregnation, intermixture, coating, solubilization, or other means. A preferred carrier substance is a mat, including fibrous mats. Mats can be made of felted, woven, or non-woven fibers and fabrics. Alternatively, the carrier substance can be made of a material selected from polymeric, ceramic, or clay materials or from any other material capable of holding a volatile material for heated volatilization. Such materials can be liquids, gels, solids (including but not limited to powders), or any other convenient physical form.

The carrier substance can be held within a container. If necessary or useful, the container can have an opening that is closed by a material through which the carrier substance cannot pass but that is permeable to the volatile material. The container can include a cup within which the carrier substance or, in some instances, the volatile material without a carrier substance, is held. The cup can have an open top closed by a material through which the carrier substance (or the volatile material prior to volatilization) cannot pass but that is permeable to the volatile material in the vapor state.

If a liquid volatile material or carrier substance is to be heated by the coil to vaporize the volatile material, the source of a volatile material can include a vessel containing the liquid volatile material or carrier substance. The apparatus then preferably includes a wick that is in contact with the liquid and extends to the vicinity of the coil to transport the liquid to the coil for heating. In this context, a wick is understood to extend to the "vicinity" of the coil if it extends sufficiently close to the coil to be heated by it with the effect of increasing volatilization of liquid carried by the wick.

In one aspect of the invention, the electric motor (preferably a nutating motor) further includes a core of magnetic material extending adjacent to the wick, with the coil being wound around at least a portion of the core. In this context, a core of magnetic material shall be defined as extending "adjacent" to the wick if it is situated immediately beside the wick, is wholly or partially contained within the wick, or is a magnetic material capable of simultaneously serving as both the wick and core, whereupon the wick and core effectively extend together.

By way of example only, such a core can usefully curve at least partially around the wick. For example, the core can be a U-shaped core, with the wick extending between and being embraced by the arms of the U. As an alternative to such a U-shaped core, the core can curve entirely around the wick one or more times, surrounding the wick. Alternatively, the core can extend parallel to the wick and embrace it to a desired extent, like a partial sheath or longitudinally extending cover.

Alternatively, a core extending "adjacent" to the wick can include a body of magnetic material contained within the wick. Such a core can be a rod-like structure held within the wick. Alternatively, the wick can include discrete particles of magnetic material distributed within the wick, the discrete particles magnetically coacting to constitute the core. Such particles can be grains or particles, filaments, or any other convenient shape. Alternatively, a wick can be made partially or entirely of woven, felted, molded, or otherwise formed magnetic material to create a wick that can serve as a core and also be either porous or at least capable of transporting liquid by capillary action. A solid material can be made with capillary grooves or channels to transport liquid as a wick. This solid material can be itself a magnetic material that can serve simultaneously as both core and wick, or it can be a non-magnetic surface material with capillary grooves, the surface material extending along or even covering at least a part of the core. Such grooves or channels are taught in a different context in Lembeck, U.S. Pat. No. 5,121,881. Lembeck shows the use of open grooves formed in a plastic surface to carry liquid by capillary action upwardly from a reservoir to another, elevated location. In Lembeck, air freshening liquid is carried upwardly from a reservoir to an evaporator pad.

The apparatus can be usefully controlled in any convenient way including, for example, by incorporating a timer or incorporating a detector for sensing a selected physical event that occurs in proximity to the apparatus and controlling the electric motor in response to sensing such event. By way of example only, temperature or light conditions or the presence of a person can all be sensed and used as triggers for control.

The invention can be summarized alternatively as being an environment control apparatus for dispensing a volatile material into ambient air including a housing having an internal chamber with an air inlet and an air outlet. The apparatus further includes an electric motor positioned within the housing and having a rotor, a coil and a conductor for applying electric current to the coil, wherein application of electric current to the coil produces heat and also produces an electromagnetic field that causes rotation of the rotor. The apparatus also includes a holder to retain the volatile material within the housing and adjacent to the coil to allow the volatile material to be heated and vaporized by heat from the coil. An air propulsion element is connected to the rotor to move air through the housing from the air inlet, across volatile material retained in the holder, and through the air outlet. Optionally, a connector can be attached to the housing and coupled to the conductor of the electric motor for connecting the environment control apparatus to an electrical outlet.

Preferably, the internal chamber of the housing of the environment control apparatus so disclosed is formed by a first section into which the air inlet opens and in which volatile material can be positioned by the holder. The first section is configured to direct air from the air inlet across the container so positioned. The housing includes a second section into which the air outlet opens and which receives air flow from the first section. Preferably, an air propulsion element driven by the rotor is located in the second section.

The environmental control apparatus as so alternatively disclosed can include a volatile material to be dispersed. The volatile material preferably is a selected air quality modification agent, pest control ingredient, allergen control agent, or combination of such materials. The environment control apparatus can include a container held by the holder, the container holding either the volatile material itself or a carrier substance into which the volatile material to be dispersed is incorporated. The container has an opening that is closed by a membrane or other material through which the as yet unvolatilized material or the carrier substance cannot pass but that is permeable to the volatile material in the vapor state. Any of the carrier substances disclosed above can be used. The wick arrangements disclosed above for use with liquid materials can be used here, as well. Similarly, the alternative forms of the coil and means of controlling the apparatus already disclosed can also be used here.

The invention can be further summarized as a refill supply of a volatile material for use with a dispensing apparatus for delivering a volatile material into ambient air, the dispensing apparatus having an electric motor having a rotor and a coil producing an electromagnetic field that causes rotation of the rotor and also producing heat when electric current is applied to the coil. The refill supply is removably attachable to the dispensing apparatus and includes a vessel containing a liquid that incorporates the volatile material; a wick in contact with the liquid and extending within the coil when the refill supply is attached to the dispensing apparatus to transport the liquid for heating by the coil; and a core of magnetic material extending adjacent to the wick and positioned within the coil when the refill supply is attached to the dispensing apparatus. Any of the alternative embodiments disclosed above of a wick with adjacently extending core can be used here.

This apparatus has the advantage that the same coil that produces an electromagnetic field that operates the motor for air propulsion also provides heat to vaporize the volatile material. This offers opportunities for compact design, efficiency of manufacture by use of fewer independent parts, and energy-efficient operation by utilizing for volatilization what would otherwise be uselessly lost coil heat.

DETAILED DESCRIPTION OF THE PREFERRED EMBODIMENTS

Figure 1:
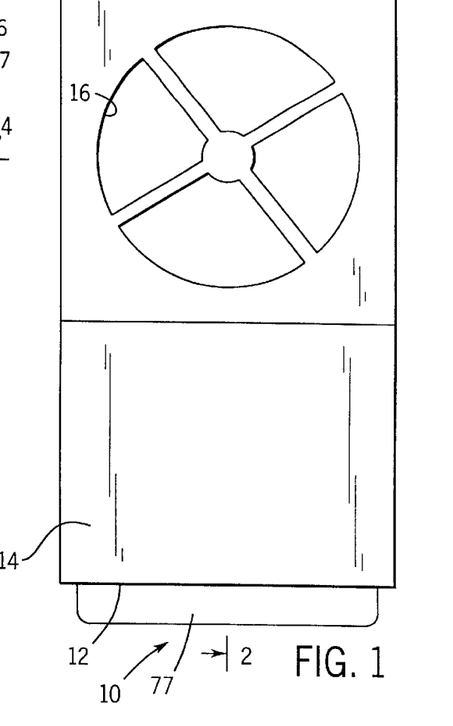
FIG. 1 is a view of the front of an apparatus for volatilizing and dispensing an air quality modification material.

With initial reference to FIG. 1, an environmental control apparatus 10 according to the present invention has a housing 12 with a front face 14 with an outlet opening 16 that extends into an interior chamber 13. Preferably the housing 12 is made of plastic, which may be molded or otherwise formed by conventional plastic fabricating techniques. The interior chamber 13 is subdivided into first and second regions 15 and 19.

Figure 2:
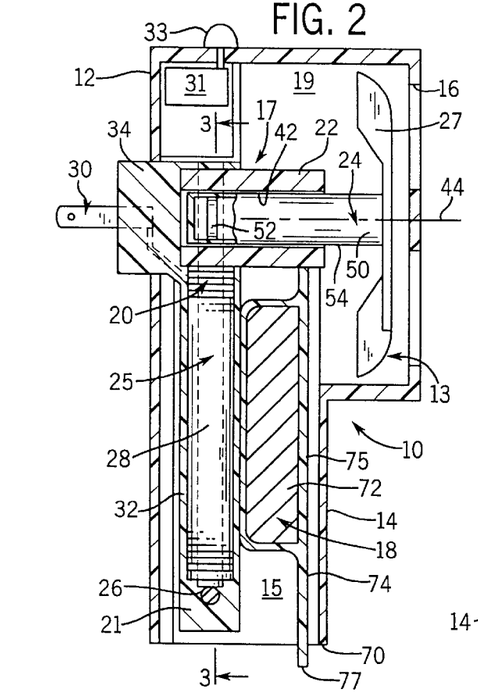
FIG. 2 is a cross-sectional view taken along line 2—2 of FIG. 1 showing the motor of the apparatus.
Figure 3:
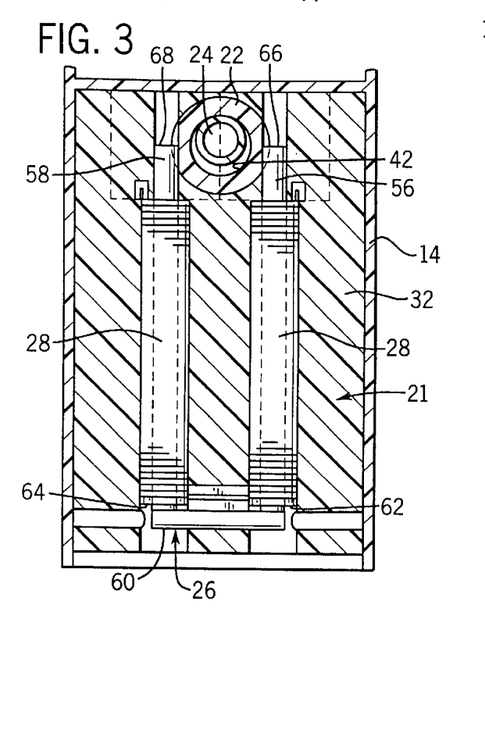
FIG. 3 is a cross-sectional view taken along lines 3—3 of FIG. 2.

As shown in FIGS. 2 and 3, the first region 15 of interior chamber 13 contains a source 18 of a volatile material to be dispersed into the environment of the apparatus 10 and the second region 19 houses a motor driven fan assembly 17. The fan assembly 17 includes a nutational motor 20 specifically adapted for driving an air impeller 27 and comprises a body 21, a stator 22, a rotor 24 and a nutational actuator 25.

While a particular, bladed impeller structure is shown, any alternative impeller adapted to cause air movement when driven by the nutational motor 20 would be within the scope and spirit of the invention. The nutational actuator 25 includes a U-shaped magnetic core 26 around which a pair of coils 28 are wound and a two pronged electrical plug 30. The coils 28 are electrically connected to the electrical plug 30, preferably in series. The body 21 of the fan assembly 17 is secured within the interior chamber 13, preferably fitting between ridges on the walls of the interior chamber 13, to hold the body in place and serve as a base for supporting a stator 22 and the nutational actuator 25.

Preferably, a circuit within the housing 12 provides a timer that controls application of electricity to the coils 28 so that the apparatus 10 operates only at certain times of the day. Alternatively, the circuit 31 can be connected to a passive infrared detector 33 that senses the presence of a person in the vicinity of the apparatus 10 and activates the motor 20 by applying electricity to the coils 28. In another version of the apparatus, the detector 33 can sense the ambient visible light and control the apparatus in response to the ambient light level. For example, the application of pesticides may be desired after dark when the target insects are prevalent. In this case, the detector 33 would be selected so as to activate the motor when the light level is below a predefined threshold. Any sensor adapted to control the application of electricity to the coils 28 in response to an environmental physical state or to an event in the vicinity of the apparatus 10 is within the scope and spirit of the invention.

In the exemplary embodiment, body 21 includes platform 32 and prong support 34. Platform 32 has apertures within which are received the stator 22, magnetic core 26 and coil 28 as best shown in FIG. 3. Prong support 34 projects rearwardly from platform 32 and holds the two prongs of plug 30 at spaced positions for insertion into a conventional electrical wall outlet. As a result, plugging apparatus 10 into an electrical wall outlet 11 simultaneously mounts the environmental control apparatus 10 to the wall. It will be apparent that alternative prong styles and plug conventions are possible and would be selected to accommodate the conventions of the country in which the device would be used and are within the scope and spirit of the invention.

The stator 22 comprises a portion of motor 20 that remains fixed with respect to nutating rotor 24. The stator provides an inner circumferential surface 42 concentric with an axis 44 about which rotor 24 nutates. Stator 22 preferably is a tubular sleeve 46 that is press fit or otherwise fastened within an aperture of platform 32 and preferably is made of a compressible material, such as rubber. Use of such a material increases the necessary friction between the stator 22 and rotor 24 and, during nutation of the rotor, dampens vibration and reduces noise.

The rotor 24 is fastened to the air impeller 27 and has a preferably hollow, non-magnetic shaft 50 with a permanent magnet 52 force fitted therein. The magnet 52 preferably is so oriented that its opposite poles are displaced along the axis 44 of rotor 24. For example, magnet 52 is oriented with a North pole facing the air impeller 27 and a South pole facing the plug 30. As will be described, the magnet 52 interacts with the magnetic forces generated by the nutational actuator 25 thereby causing rotor 24 to nutate about axis 44 against circumferential surface 42 of stator 22.

The shaft 50 has an outer circumferential surface 54 adjacent the inner circumferential surface 42 of stator 22, which stator surface extends concentrically about axis 44. The diameter of shaft 50 is less than the inner diameter of stator 22 defined by inner circumferential surface 42. In the exemplary embodiment, the ratio of the inner diameter of the stator bore to the outer shaft diameter is approximately 1.0 to 1.2. It has been found that as the mass of rotor 24 and the attached component are increased, the ratio of the inner bore diameter to the outer shaft diameter should be decreased.

The U-shaped magnetic core 26 generally includes legs 56 and 58, a cross member 60, and electrical insulators 62 and 64. Legs 56 and 58 and the cross member 60 comprise an elongated material preferably having a high magnetic susceptibility, such as ferromagnetic materials including ferrite, cobalt, nickel and gadolinium. Electrical insulators 62 and 64 extend between legs 76 and 78 and coils 28. Legs 56 and 58 include end portions 66 and 68, respectively, which are positioned on opposite sides of rotor 24 and are angularly spaced from one another in relation to the shaft 50 by approximately 180 degrees. The opposite ends of legs 56 and 58 are interconnected to one another by the cross member 60, which conducts magnetic flux across legs 56 and 58 when magnetic core 26 is magnetized by alternating current flowing through coils 28.

Each coil 28 encircles one of the legs 56 or 58, with the coils encircling the legs in the same direction to create reinforcing rather than canceling magnetic flux in the combined legs 56 and 58 and cross member 60. As shown by FIG. 3, the coils 28 have ends adjacent to the rotor 22 that are electrically connected to the prongs of the electrical plug 30. The opposite ends of each coil 28, adjacent the cross member 60, are electrically connected together.

When plug 30 is inserted into a standard electrical outlet, alternating electric current flows through both coils 28 to produce a magnetic flux that flows through the legs 56 and 58. This produces opposite magnetic poles at the ends of the core 26 on opposite sides of the rotor. Because the electrical current is alternating, the core end portions 66 and 68 alternate between North and South magnetic poles at the frequency of the alternating current. This results in an alternating attraction and repulsion of the North and South poles of magnet 52 in rotor 24, creating an alternating torque that causes the rotor to wobble or nutate about axis 44. In particular, the resulting alternating attraction and repulsion of rotor 24 initially causes portions of rotor 24 to reciprocate between opposite sides of circumferential surface 42. However, during this reciprocation, rotor 24 has a tendency to become off-centered so that the rotor begins reciprocating between portions of stator surface 42 that are other than 180 degrees apart, striking the circumferential surface 42 a somewhat glancing blow each time. Consequently, the alternate attraction and repulsion causes rotor 24 to roll against circumferential surface 42 and nutate about axis 44.

It is believed that the magnetic field, attracting and repelling the rotor 24, must have a sufficient magnitude to ensure that rotor becomes off-centered during reciprocation and that the desirable magnetic field magnitude is dependent upon the rotor's mass and the relative diameters of the stator 22 and the rotor 24. The speed at which rotor 24 rotates is dependent upon the frequency at which rotor 24 is attracted and repelled and upon the relative diameter of stator 22 and rotor 24.

With reference to FIG. 2, rotation of the air impeller 27 draws air through the interior of housing 12 preferably upwardly from an inlet at end 70, past a source 18 of a volatile material, and through the outlet opening 16. An opposite air flow direction is also possible. Although the air impeller 27 is illustrated as a multiple blade fan, other types of devices that can be motor driven for creating that movement of air may be utilized. The first region 15 of interior housing chamber 13 acts as a chimney directing the air flow past the volatile source 18. That air flow picks up the vapors emitted from the source 18 and disperses the volatile material into the room in which the apparatus is located.

The volatile source 18 comprises a carrier substance 72, such as a gel that either constitutes or has been impregnated with the volatile material to be dispensed. In the exemplary embodiment, the carrier substance 72 is held in a container 74 at least a portion of which is either open or at least (and preferably) is closed by a barrier that contains the carrier substance 72 but is permeable to the vapor of the volatile material being used. For example, the container 74 has a membrane 75 along one side through which vapors pass. Although the container 74 is preferably made of a heat-resistive plastic, metal or other suitably heat-resistive and volatile containing materials may be used.

In the exemplary embodiment shown, the container 74 slides through the open end 70 of the housing 12 and into a holder in the first region 15 where it is retained by friction. When sufficient material has been volatilized from the carrier substance 72, the source 18 can be replaced with a new one by pulling on a tab 77 that projects outward from the container and through the open housing end 70. Although the arrangement shown is preferred, alternative structures to introduce, hold, and remove or replace a container will be apparent to one skilled in the art. For example, a housing can be designed with two open ends such that fresh containers can be introduced through one of the open ends and simply push an exhausted container out of the other open end.

As an alternative to an impregnated gel, the volatile material can be contained in other types of carrier substances, some of which require no separate container such as container 74. Such carrier substances include fibrous mats of felted, woven, or non-woven fabrics; molded, extruded, cast, or otherwise formed polymeric, ceramic, and clay materials; as well as other convenient materials loaded with volatile ingredients, whether by impregnation, printing or otherwise. When present, the container can be a metal or plastic cup holding a volatilizable gel, powder, or liquid that can either be adhered to the cup or be retained in the cup by a volatile-permeable membrane, grid, or other suitable barrier that retains the volatilizable material or carrier substance but that is permeable to the volatile. Indeed, the carrier substance or carrier substance in a container can be any convenient means for holding a material to be volatilized by the application of heat. The art is well aware of a wide variety of suitable materials and structures used in conventional mosquito-control heated devices and in air-scenting devices.

In addition to causing nutational movement of rotor 24 about axis 44 of stator 22, the nutational actuator 25 formed by magnetic core 26, coils 28 and plug 30 also serves as a heat source to volatilize the material within the source 18. Owing to the inherent resistance of their electrically conductive material, the coils 28 heat up in response to the current flowing through them. By so designing the apparatus 10 that the coils 28 extend along and in close proximity to the carrier substance 72, the heat generated in the coils is transferred to the source 18 and warms the volatile material. The size and configuration of the nutational actuator 25 preferably conform to the size and shape of the source to enhance the heating effect. This action heats the volatile material above its volatilization temperature thereby producing vapors that are picked-up by the air flow through the first internal chamber region 15. By using the motor coils 28 to heat the volatile material, a separate heating element is not required and the apparatus 10 can be more compact, less expensive to manufacture, and more energy efficient.

Figure 4:
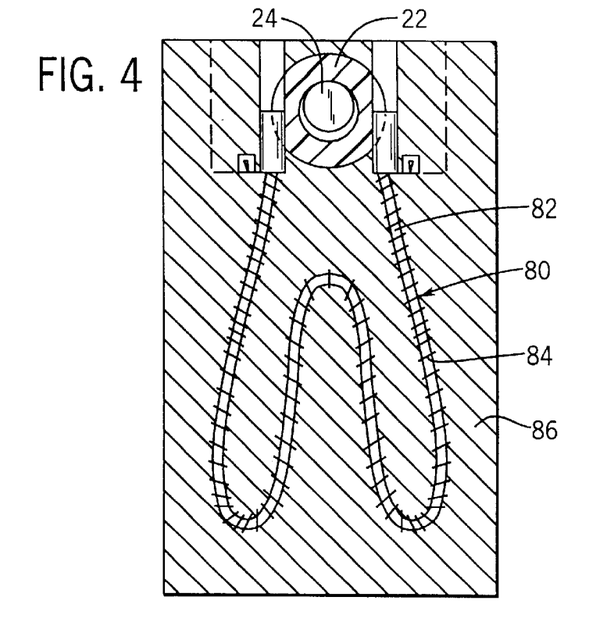
FIG. 4 is a cross-sectional view similar to FIG. 3, illustrating a variation of a coil for the motor.

FIG. 4 illustrates an alternative embodiment of the nutational actuator 80, which is mounted in a body 86 that serves the same function as body 21 in FIGS. 2 and 3. The nutational actuator 80 comprises a bendable core 82 of magnetic material and a single coil 84 wound around substantially the entire length of the core 82. Their bendable nature allows the core and coil to have a serpentine shape that extends through a greater portion of the body 86 and thus extends adjacent a greater surface area of the carrier substance 72. This more evenly distributes the heat from the coils to the carrier substance and the volatile material.

Figure 5:
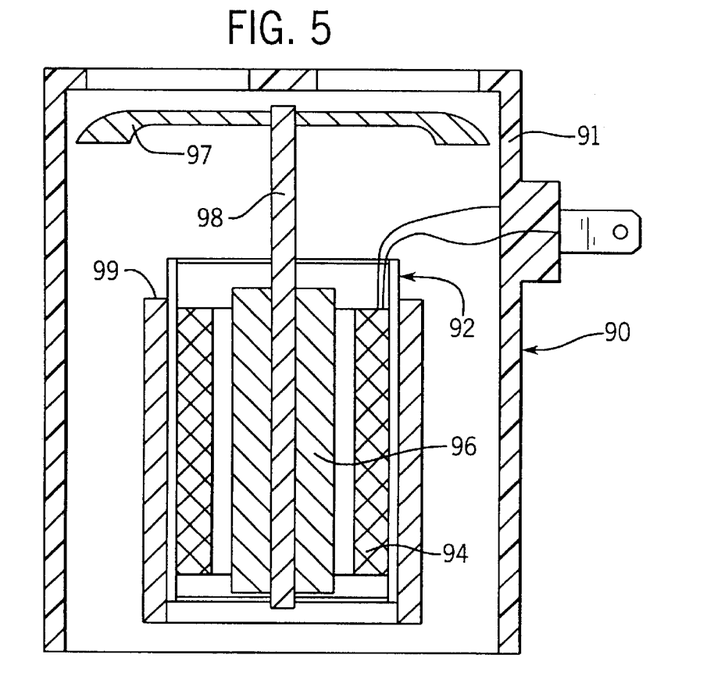
FIG. 5 is a cross-sectional view through a second embodiment of an apparatus for volatilizing and dispensing a chemical.

With reference to FIG. 5, the present concept can be applied to a dispersing apparatus 90 that utilizes a standard, non-nutating electric motor such as the electric motor shown at 92. The electric motor 92 is located within a housing 91 and includes a hollow cylindrical stator coil 94 within which a conventional permanent magnet rotor 96 is mounted. The rotor 96 is coupled to a shaft 98 with an air impeller 97 attached thereto.

Figure 6:
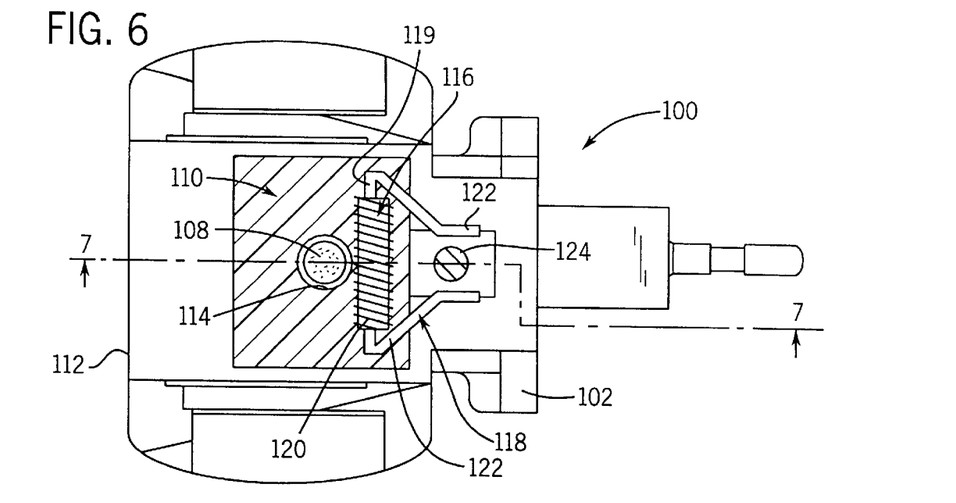
FIG. 6 depicts a horizontal cross-section through a third embodiment of an apparatus for volatilizing and dispensing a liquid chemical.
Figure 7:
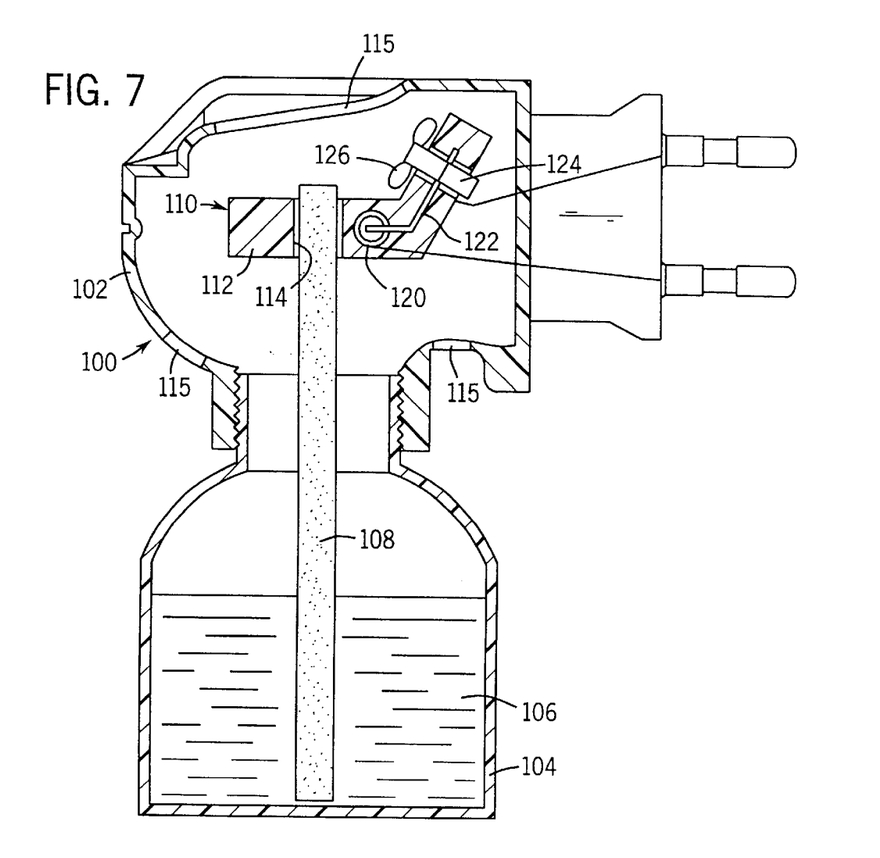
FIG. 7 is a cross-sectional view taken along line 7—7 of FIG. 6.

In the embodiment shown in FIG. 5, the volatile material is contained in a tubular carrier 99 that is pushed around the outer diameter of the stator coil 94 and held in place, preferably simply by friction. The carrier 99 has a structure similar to that of the previously described source 18. Alternatively, other shapes and mounting configurations of the carrier can be utilized with this motor design so long as the carrier is placed in relation to the coil 94 such that the heat of the coil effectively heats the carrier to volatilize the material to be dispensed.

When the dispersing apparatus 90 is plugged into a standard electrical outlet, an electromagnetic field produced by the stator coil 94 causes the rotor 96, shaft 98 and air impeller 97 to spin. This creates a flow of air through the housing 91 and across the carrier 99. The flow of electric current through the stator coil 94 also generates heat that raises the temperature of the carrier and vaporizes the volatile material therein. The vapors from that material are drawn into the air flow through the housing and exhausted into the ambient environment.

Referring to FIGS. 6 and 7, the present invention also can be used with volatile materials in liquid form. The apparatus 100 for this purpose comprises a motor housing 102 that attaches to a vessel 104 that contains the liquid volatile material 106. A wick 108 projects preferably upwardly from within the vessel and into the motor housing 102.

A motor assembly 110 is mounted within the housing 102 and has a body 112 with an aperture 114 through which the wick 108 extends. A nutational actuator 116 includes a magnetic core 118 with a linear section 119 around which an electromagnet coil 120 is wound. The wick, which is in contact with the liquid volatile material 106, extends to the vicinity of the coil 120 to transport the liquid to the coil for heating. The linear section 119 of the magnetic core 118 is located adjacent the aperture 114, and a pair of arms 122 of the core extends from ends of the linear section 119 to opposite sides of a rotor 124. A propeller-type fan 126 or alternative air impeller is attached to the rotor 124.

Figure 8:
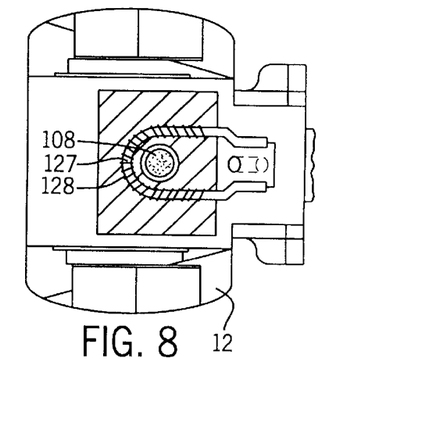
FIG. 8 is a cross-sectional view similar to that of FIG. 8 depicting an alternative coil arrangement.

Alternatively as shown in FIG. 8, the nutational actuator may have a U-shaped magnetic core 127 and electromagnet coil 128. The curved core 127 and coil 128 extend at least partially around the wick 108 of the source of volatile material. This latter configuration increases exposure of the wick 108 to heat produced by the coil 128. Alternatively, the core 127 and coil 128 may loop multiple times around the wick 108.

Referring again to FIGS. 6 and 7, the wick 108 draws the liquid volatile material 106 from the vessel 104 into the motor assembly 110. When electricity is applied to the apparatus 100, the nutational actuator 116 causes the rotor and the fan 126 to spin, which action causes air to flow through apertures 115 in the housing 102. The heat from the coil 120 is transferred to the upper end of the wick 108 to volatilize the volatile material at that end. The vapors from the volatile material are carried into the ambient environment by the air flow generated by the fan 126.

Figure 9:
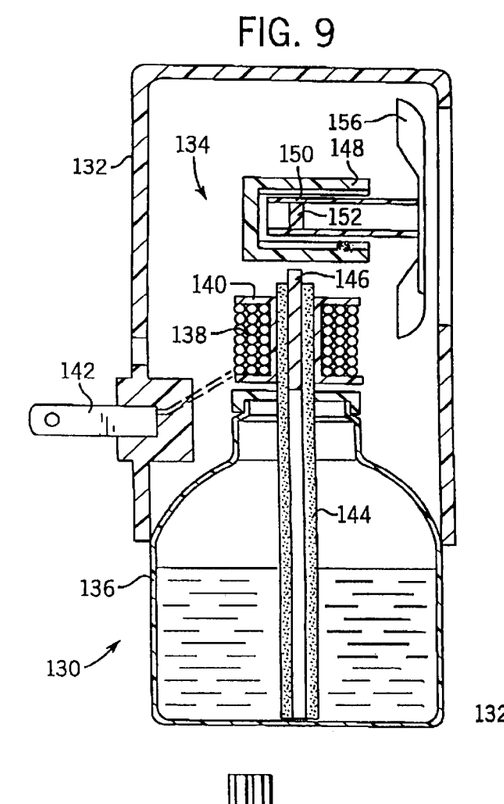
FIG. 9 depicts a vertical cross-section through a fourth embodiment of an apparatus for volatilizing and dispensing a liquid chemical.

FIG. 9 shows another embodiment of an apparatus 130 for volatilizing and dispersing a liquid volatile material. A housing 132 attaches to a vessel 136 containing the volatile material. The housing 132 encloses a nutational motor 134 that comprises an annular coil 138 wound on a bobbin 140 and electrically connected to a two-pronged plug 142. A wick 144 extends from within the vessel 136 through a center opening in the bobbin and coil assembly and receives heat from the coil 138 when the motor is operating.

A rod-like core 146 of magnetic material is held within the portion of the wick 144 that is within the bobbin 140 and coil 138. The core 146 projects toward a stator 148 within which is a rotor 150 of the nutational motor 134. The rotor 150 contains a permanent magnet 152 and has a fan 156 or other air impeller attached to one end. The alternating magnetic flux produced by the coil 138 is conducted by the rod-like core 146 and applied to the stator 148. That action produces nutation of the rotor 150 and rotation of the fan 156.

Figure 10:
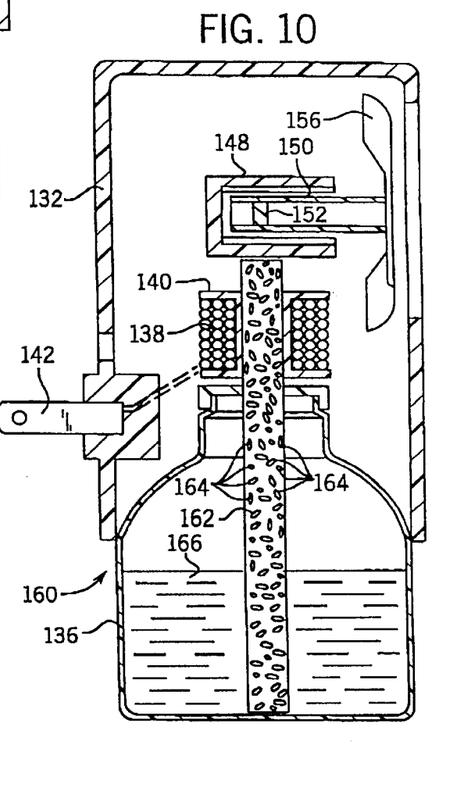
FIG. 10 depicts a vertical cross-section through a fifth embodiment of an apparatus for volatilizing and dispensing a liquid chemical.

FIG. 10 illustrates a modification of the embodiment of apparatus 130 in FIG. 9, and identical components have been assigned the same reference numerals. In the resultant apparatus 160, the wick 144 and core 146 have been replaced by a wick 162 that is impregnated with discrete particles 164 of a magnetic material. The discrete magnetic particles 164 coact to form the core for the electric motor. The discrete magnetic particles may be granular, as shown, or they may be filaments or otherwise vary in shape. Thus the wick 162 both draws the liquid volatile material 166 from the vessel 136 to the coil 138 for heating and serves as the core to transfer magnetic flux from the coil to the stator 148.

Figure 11:
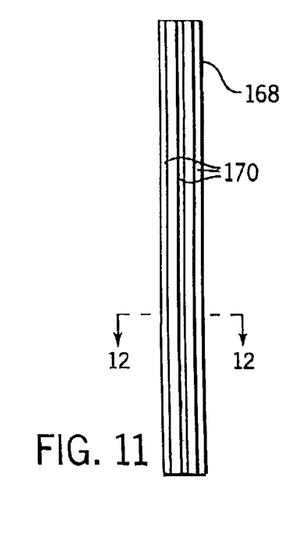
FIG. 11 depicts a wick made of a solid material and having capillary grooves or channels to transport liquid.
Figure 12:
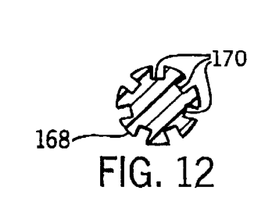
FIG. 12 is a cross-sectional view of the wick of FIG. 11, taken along section line 12—12 of FIG. 11.

FIG. 11 illustrates an alternative embodiment of a wick, wick 168, generally corresponding in mode of use to wick 162 of FIG. 10. FIG. 12 is a cross-sectional view of wick 168. Wick 168 is made of a generally solid material and has capillary grooves 170, which are open-faced channels, to transport liquid typically upwardly from a vessel (not shown) corresponding to vessel 136 of FIG. 10 to a coil (not shown) corresponding to coil 138 of FIG. 10. The solid material of which the wick 168 is made may itself be or include a magnetic material. For example, it may be a plastic incorporating a ferromagnetic material introduced as a powder before the plastic hardens. Alternatively, the solid material can be non-magnetic and either extend along or cover a core made of a magnetic material. The wick 168 can be made by any conventional plastic manufacturing techniques appropriate to such structures, including molding, extrusion, machining, and the like.

The foregoing description was primarily directed to preferred embodiments of the invention. Although some attention was given to various alternatives within the scope of the invention, it is anticipated that one skilled in the art will likely realize additional alternatives that are now apparent from disclosure of embodiments of the invention. Accordingly, the scope of the invention should be determined from the following claims and not limited by the above disclosure.

INDUSTRIAL APPLICABILITY

Volatilizing scents, insect control materials, and other volatile materials is an established, useful practice. The invention disclosed provides for an apparatus that provides a new means for doing so effectively.

What is claimed is:

1. An apparatus for dispensing a volatile material into ambient air, said apparatus comprising:
   an electric motor having a rotor and a coil that produces an electromagnetic field causing rotation of the rotor, and that produces heat when electric current is applied to the coil;
   a source of the volatile material adjacent to the coil wherein the volatile material is vaporized by the heat when electric current is applied to the coil without requiring an additional heat source; and
   an air propulsion element connected to the rotor to move air and blow the volatile material away from the source.

2. The apparatus as recited in claim 1 wherein the electric motor comprises a nutating type motor.

3. The apparatus as recited in claim 1 wherein the air propulsion element comprises a fan.

4. The apparatus as recited in claim 1 wherein the volatile material is selected from the group consisting of air quality modification agents, pest control ingredients, and allergen control agents.

5. The apparatus as recited in claim 1 wherein the source of a volatile material comprises a carrier substance into which the volatile material is incorporated.

6. The apparatus as recited in claim 5 wherein the carrier substance is a fibrous mat.

7. The apparatus as recited in claim 5 wherein the carrier substance is made of a material selected from the group consisting of fibrous, polymeric, ceramic, clay, gel, and liquid materials.

8. The apparatus as recited in claim 5 including a container that holds the carrier substance.

9. The apparatus as recited in claim 8 wherein the container has an opening that is closed by a material through which the carrier substance cannot pass but that is permeable to the volatile material.

10. The apparatus as recited in claim 1 wherein the source of a volatile material comprises a vessel containing a liquid that incorporates the volatile material, and wherein the liquid is heated by the coil to vaporize the volatile material.

11. The apparatus as recited in claim 10 including a wick that is in contact with the liquid and extends to the vicinity of the coil to transport the liquid to the coil for heating.

12. The apparatus as recited in claim 11 wherein the electric motor further comprises a core of magnetic material extending adjacent to the wick, and wherein the coil is wound around the core.

13. The apparatus as recited in claim 12 wherein the core of magnetic material curves at least partially around the wick.

14. The apparatus as recited in claim 11 wherein the core includes a body of magnetic material contained within the wick.

15. The apparatus as recited in claim 11 wherein the wick includes discrete particles of magnetic material distributed within the wick, the discrete particles magnetically coacting to constitute the core.

16. The apparatus as recited in claim 11 wherein the electric motor further comprises a U-shaped core of magnetic material on which the coil is wound, the U-shaped core having two arms between which the wick extends.

17. The apparatus as recited in claim 1 wherein the electric motor further comprises a curved core of magnetic material on which the coil is wound, the curved core extending at least partially around the source of volatile material.

18. The apparatus as recited in claim 1 wherein the coil has a serpentine shape.

19. The apparatus as recited in claim 1 further comprising a timer connected to the electric motor and applying electricity to the electric motor during predefined intervals.

20. The apparatus recited in claim 1 further comprising a detector for sensing the presence of a person within a given area and controlling the electric motor in response to sensing such presence.

21. The apparatus as recited in claim 1 further comprising a detector for sensing a level of light impinging on the detector and controlling activation of the electric motor in response to sensing the level of light.

22. The apparatus as recited in claim 1 further comprising a detector for sensing a physical event that occurs in proximity to the apparatus and controlling the electric motor in response to sensing such event.

23. An environment control apparatus for dispensing a volatile material into ambient air, said environment control apparatus comprising:
    a housing having an internal chamber with an air inlet and an air outlet;
    an electric motor positioned within the housing and having a rotor, and a coil, wherein application of electric current to the coil produces heat and also produces an electromagnetic field that causes rotation of the rotor without requiring an additional heat source;
    a holder to retain a container of the volatile material within the housing and adjacent to the coil thereby allowing the volatile material to be heated and vaporized by heat from the coil; and
    an air propulsion element connected to the rotor to move air through the housing from the air inlet, across a carrier retained in the holder, and through the air outlet.

24. The environment control apparatus as recited in claim 23 further comprising a connector attached to the housing and electrically coupled to the coil of the electric motor for connecting the environment control apparatus to an electrical outlet.

25. The environment control apparatus as recited in claim 23 wherein the internal chamber of the housing is formed by:
    a first section into which the air inlet opens and in which volatile material can be positioned by the holder, wherein the first section is configured to direct air from the air inlet across the container so positioned; and
    a second section into which the air outlet opens and which receives air flow from the first section, wherein the an air propulsion element is located in the second section.

26. The environment control apparatus as recited in claim 23 including a volatile material to be dispersed and wherein the volatile material is selected from a group consisting of air quality modification agents, pest control ingredients, and allergen control agents.

27. The environment control apparatus as recited in claim 23 including a container held by the holder, the container holding a carrier substance into which the volatile material to be dispersed is incorporated, the container having an opening that is closed by a membrane through which the carrier substance cannot pass but that is permeable to the volatile material.

28. The environment control apparatus as recited in claim 27 wherein the carrier substance is one of a liquid, a gel, and a solid.

29. The environment control apparatus as recited in claim 23 including a carrier of the volatile material to be dispersed, the carrier being held by the holder, and wherein the carrier of the volatile material comprises a vessel containing a liquid that incorporates the volatile material, and wherein the liquid is heated by the coil to volatilize the volatile material.

30. The environment control apparatus as recited in claim 29 wherein a wick transports the liquid to the vicinity of the coil for heating.

31. The environment control apparatus as recited in claim 23 wherein the coil has a serpentine shape.

32. The environment control apparatus as recited in claim 23 wherein the coil is wound on a core that has a U-shape.

33. The environment control apparatus as recited in claim 23 further comprising a detector for sensing a physical event in proximity to the apparatus and controlling the electric motor in response to sensing such event.

34. A refill supply of a volatile material for use with a dispensing apparatus for delivering a volatile material into ambient air, the dispensing apparatus having an electric motor having a rotor and a coil producing an electromagnetic field that causes rotation of the rotor and also producing heat when electric current is applied to the coil, the refill supply being removably attachable to the dispensing apparatus and comprising:
    a vessel containing a liquid that incorporates the volatile material;
    a wick in contact with the liquid and extending within the coil when the refill supply is attached to the dispensing apparatus to transport the liquid for heating by the coil; and
    a core of magnetic material extending adjacent to the wick and positioned within the coil when the refill supply is attached to the dispensing apparatus.

35. The refill supply as recited in claim 34 wherein the core includes a body of magnetic material contained within the wick.

36. The refill supply as recited in claim 34 wherein the wick includes discrete particles of magnetic material distributed within the wick, and the discrete particles magnetically coacting to constitute the core.

37. The refill supply as recited in claim 34 wherein the wick includes magnetic material that is woven, felted, or otherwise formed to create a wick that can serve as a core and that also has capillary passageways capable of transporting liquid.

38. The refill supply as recited in claim 34 wherein the wick includes a solid material having capillary grooves or channels to transport liquid.

39. The refill supply as recited in claim 38 wherein the solid material is made of a magnetic material.

40. The refill supply as recited in claim 38 wherein the solid material is non-magnetic and extends along the core.

41. The refill supply as recited in claim 38 wherein the solid material is non-magnetic and covers at least a portion of the core.

* * * * *